US006197229B1

(12) United States Patent
Ando et al.

(10) Patent No.: US 6,197,229 B1
(45) Date of Patent: Mar. 6, 2001

(54) METHOD FOR HIGH SUPERCOILED DNA CONTENT MICROSPHERES

(75) Inventors: Shuicho Ando, Brookline; David Putnam, Cambridge; Robert S. Langer, Newton, all of MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/209,032

(22) Filed: Dec. 10, 1998

Related U.S. Application Data

(60) Provisional application No. 60/069,358, filed on Dec. 12, 1997.

(51) Int. Cl.[7] .............................. B01J 13/02; B01J 13/04
(52) U.S. Cl. ......................... 264/4.1; 264/4.3; 264/4.33; 264/4.4; 264/4.6
(58) Field of Search ........................... 264/4.1, 4.3, 4.33, 264/4.6, 4.4

(56) References Cited

U.S. PATENT DOCUMENTS

| | | | | |
|---|---|---|---|---|
| 3,885,011 | * | 5/1975 | Renoux et al. | 424/92 |
| 5,075,109 | * | 12/1991 | Tice et al. | 424/88 |
| 5,407,609 | * | 4/1995 | Tice et al. | 264/46 |

FOREIGN PATENT DOCUMENTS

| | | | |
|---|---|---|---|
| 266119 B1 | * | 7/1994 | (EP) . |
| WO95/24929 | * | 9/1995 | (WO) . |
| WO97/03702 | * | 2/1997 | (WO) . |
| WO97/17063 | * | 5/1997 | (WO) . |
| WO98/31398 | * | 7/1998 | (WO) . |
| WO98/51279 | * | 11/1998 | (WO) . |

OTHER PUBLICATIONS

Jong Y.S. et al. "Controlled Release of Plasmid DNA" *Journal of Controlled Release*, 1997, 47, 123–124.*
Crystal, R.G., "The Gene as the Drug", *Nature Medicine*, 1995, 1, 15.*
Jones et al., "Poly(DL–lactide–co–glycolide)–Encapsulated Plasmid DNA Elicits Systemic and Muscosal Antibody Responses to Encoded Protein after Oral Administration", *Vaccine*, 1997, 15, 814.*
Langer, R., "New Methods of Drug Delivery", *Science*, 1990, 249, 1527.*
Mathiowitz et al., "Biologically Erodable Microspheres as Potential Oral Drug Delivery Systems", *Nature*, 1997, 386, 410.*
Miller, A.D., "Human Gene Therapy Comes of Age", *Nature*, 1992, 357, 455.*
Mulligen, R.C., "The Basic Science of Gene Therapy", *Science*, 1993, 260, 926.*

* cited by examiner

*Primary Examiner*—Nathan M. Nutter
(74) *Attorney, Agent, or Firm*—Choate, Hall & Stewart

(57) ABSTRACT

A method for formulation of high supercoiled DNA content microspheres is described herein. A primary emulsion is formed which optionally contains a DNA nicking inhibitor in addition to DNA with or without buffer. The temperature of the primary emulsion is lowered below the freezing point of the aqueous inner phase which provides increased encapsulation efficiency by decreasing the rate of diffusion of DNA out of the aqueous phase. Thereafter, the primary emulsion is transferred to a water-based surfactant solution and subjected to homogenization to form a secondary microsphere emulsion. The organic phase is removed and the microspheres hardened which are then isolated, frozen and lyophilized.

32 Claims, 10 Drawing Sheets

AGAROSE GEL ELECTROPHORESIS OF DNA IN MICROSPHERES (MS) (N = 3). FROM LEFT TO RIGHT, LANES 1 AND 11: 1 kb LADDER; LANES 2-4: INITIAL DNA; LANES 5-7: DNA IN MS BEFORE LYOPHILIZATION; LANES 8-10: DNA IN MS AFTER LYOPHILIZATION.

FIG. 4

EFFECT OF EXCIPIENTS ON RETAINING SUPERCOILED DNA (S.C.DNA) UNDER MICROSPHERE PROCEDURE SUCH AS HOMOGENIZATION AND LYOPHILIZATION. SAMPLES WERE PREPARED BY CRYOPREPARATION, AND THE HOMOGENIZATION RATE WAS 7000 rpm FOR 14 SEC. (N=3)

| | S.C.DNA REMAINING (INITIALS % ± SD) | |
|---|---|---|
| | BEFORE LYOPHILIZATION | AFTER LYOPHILIZATION |
| WATER | 42.3 ± 0.7 | 39.0 ± 4.2 |
| 1 mM EDTA SOLUTION, pH 7.5 | 78.2 ± 1.7 | 68.3 ± 3.6 |
| PHOSPHATE BUFFERED SALINE, pH 7.5 | 49.1 ± 4.8 | 19.8 ± 0.4 |
| 300 mM LACTOSE SOLUTION, pH 7.5 | 41.7 ± 2.4 | 20.8 ± 1.3 |
| 300 mM LACTOSE/1 mM EDTA SOLUTION, pH 7.5 | 95.1 ± 0.7 | 88.6 ± 1.9 |

FIG.5

EFFECT OF HOMOGENIZATION RATE, CRYOPREPARATION AND ADDITION OF EDTA ON REMAINING SUPERCOILED DNA (S.C.DNA) (N=3).

S.C. DNA REMAINING (INITIAL % ± SD)

| DNA SOLUTION | HOMOGENIZATION RATE | | |
|---|---|---|---|
| | 5000 rpm | 7000 rpm | 9000 rpm |
| WATER WITHOUT CRYOPREPARATION | 36.9 ± 1.9 | 26.1 ± 3.6 | 20.1 ± 3.4 |
| WATER WITH CRYOPREPARATION | 54.4 ± 1.1 | 46.2 ± 0.7 | 37.3 ± 4.7 |
| EDTA$^{\alpha}$ WITHOUT CRYOPREPARATION | 68.4 ± 1.9 | 47.0 ± 2.6 | 40.6 ± 0.3 |
| EDTA$^{\alpha}$ WITH CRYOPREPARATION | 92.2 ± 1.3 | 75.5 ± 2.1 | 64.7 ± 3.5 |

$\alpha$ 1 mM EDTA, pH 7.5

FIG. 6

EFFECT OF EXCIPIENTS ON RETAINING SUPERCOILED DNA (S.C.DNA). SAMPLES WERE PREPARED BY CRYOPREPARATION; HOMOGENIZATION RATE = 7000 rpm, 14 SEC. (N=3)

| DNA SOLUTION | S.C.DNA REMAINING (INITIAL % ± SD) |
|---|---|
| WATER | 46.2 ± 0.7 |
| 1 mM EDTA SOLUTION, pH 7.5 | 75.5 ± 2.1 |
| 1 mM CALCIUM IONOPHORE II | 36.1 ± 0.8 |
| 10 mM TRIS BUFFER, pH 7.5 | 40.5 ± 2.5 |
| PHOSPHATE BUFFERED SALINE, pH 7.5 | 36.1 ± 3.5 |
| 300 mM LACTOSE SOLUTION, pH 7.5 | 39.6 ± 2.7 |
| 1 mM EDTA/10 mM TRIS BUFFER, pH 7.5 | 62.1 ± 2.7 |
| 1 mM EDTA/PHOSPHATE BUFFERED SALINE, pH 7.5 | 68.2 ± 5.2 |
| 300 mM LACTOSE/1 mM EDTA SOLUTION, pH 7.5 | 94.5 ± 1.0 |
| 300 mM LACTOSE/1 mM EDTA/10 mM TRIS BUFFER, pH 7.5 | 86.2 ± 3.6 |

FIG. 7

EFFECT OF LYOPHILIZATION ON RETAINING SUPERCOILED DNA (S.C.DNA). DNA SAMPLES WERE DIRECTLY LYOPHILIZED WITHOUT THE PRESENCE OF PLGA OR UNDERGOING MICROSPHERE PREPARATIONS.

| DNA SOLUTION | S.C.DNA REMAINING (INITIAL % ± SD) |
|---|---|
| WATER | 97.9 ± 1.0 |
| 1 mM EDTA SOLUTION, pH 7.5 | 95.2 ± 0.6 |
| 10 mM TRIS BUFFER, pH 7.5 | 70.1 ± 2.5 |
| PHOSPHATE BUFFERED SALINE, pH 7.5 | 42.5 ± 3.8 |
| 300 mM LACTOSE SOLUTION, pH 7.5 | 95.8 ± 0.4 |
| 1 mM EDTA/10 mM TRIS BUFFER, pH 7.5 | 73.0 ± 0.8 |
| 1 mM EDTA/PHOSPHATE BUFFERED SALINE, pH 7.5 | 47.4 ± 2.6 |
| 300 mM LACTOSE/1 mM EDTA SOLUTION, pH 7.5 | 95.6 ± 0.6 |

(DNA IN TE BUFFER WITH INCREASING
SACCNARIDE CONCENTRATION)

○ : GLUCOSE

□ : LACTOSE

△ : SUCROSE

AGAROSE GEL ELECTROPHORESIS OF DNA INCUBATED AT ROOM TEMPERATURE
IN PBS AT pH 7.4 (LANES 1-4) AND pH 4.0 (LANES 5-7) FOR 0-(LANE 1),
10 (LANES 2, 5), 30 (LANES 3, 6), OR 60 (LANES 4, 7)MIN.

MATERIALS

PLASMID DNA: pCMV-βGAL (7.2kpb, PURIFIED IN E. COLI. DH5α)
BIODEGRADABLE POLYMER: PLGA (50:50, RESOMER RG503 MW 30,000)
EMULSIFIER: POLY (VINYL ALCOHOL)(PVA)(MW 25,000, 88% MOL HYDROLYZED)

FIG.10

ANALYTICAL METHODS

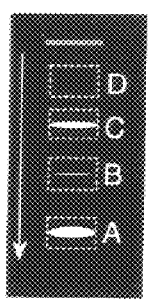

DNA STRUCTURE ANALYSIS: GEL ELECTROPHORESIS (1% AGAROSE CONTAINING ETHIDIUM BROMIDE)
SEMI-QUANTITATION OF SUPER COILED DNA: BIO RAD GEL DOC 1000 (MOLECULAR ANALYST 2.1)

AS SHOWN IN FIG. 1, AFTER MS FORMATION, DNA WAS EXTRACTED AND ANALYZED BY AGAROSE GEL ELECTROPHORESIS EACH DNA WAS INTEGRATED AS A VOLUME.
THE VOLUME INTEGRATED FROM THE SUPER COILED DNA (S.C.DNA) BAND AGAINST THE TOTAL VOLUMES INTEGRATED FROM ALL BANDS WAS ASSUMED AS S.C.DNA RATIO.
S.C.DNA REMAINING (INITIAL %) WAS CALCULATED AS FOLLOWS.
S.C.DNA REMAINING (INITIAL %) = 100 × S.C.DNA RATIO OF SAMPLES/S.C.DNA RATIO OF INITIAL DNA
S.C.DNA RATIO = (S.C.DNA VOLUME − BACKGROUND VOLUME)/(S.C.DNA VOLUME + LINEAR DNA VOLUME + VOLUME + LINEAR DNA VOLUME + NICKED DNA VOLUME − 3 × BACKGROUND VOLUME)

SCHEMATIC REPRESENTATION OF AGAROSE GEL ELECTROPHORESIS OF DNA; A) SUPER COILED DNA, B) LINEAR DNA, C) NICKED DNA AND D) BACKGROUND

MS DIAMETER WAS MEASURED USING A COULTER MULTISIZER II
PLASMID DNA CONTENT IN MS WAS DETERMINED BY FLUOLOSPECTROSCOPY USING A PICOGREEN REAGENT ASSAY

MS MANUFACTURING PROCEDURES

WATER-IN OIL-IN WATER DOUBLE EMULSION METHOD

METHOD FOR HIGH SUPERCOILED DNA CONTENT MICROSPHERES

This application claims priority to the co-pending provisional application entitled "Method for High Supercoiled DNA Content Microspheres" 60/069,358 filed on Dec. 12, 1997, which is incorporated in its entirety by reference.

BACKGROUND OF THE INVENTION

The importance of DNA based therapeutics, in particular in gene therapy, has led to increased research and development in this area (see, for example, Friedmann, T. *Science*, 1989, 244, 1275; Miller, A. D. *Nature*, 1992, 260, 455; Mulligan, R. C. *Science*, 1993, 260, 926; Wilson, J. M. *Nature*, 1993, 365, 691; Crystal, R. G. *Nature Med.*, 1995, 1, 15). The use of these therapeutics can be problematic, however, because during drug delivery the DNA is subject to degradation. To maximize the power of these agents, it would be desirable to develop a mode of delivery in which the DNA-based therapeutic is protected from degradation.

Towards this end, several nano- or micro-encapsulation techniques have been developed and have been described in the literature (see, for example, Langer, R. S. *Science* 1990, 249, 1527; Kato et al. *J Biol. Chem.* 1991, 266, 3361; Jong et al., *J. Controlled Release* 1997, 47, 123; Mathiowitz et al., *Nature* 1997, 386, 410; Smith et al. *Adv. Drug Del. Rev.* 1997, 26, 135). Additionally, U.S. Pat. No. 5,407,609 by Tice et al. describes a method of microencapsulating biological or immunological agents to form a microencapsulated product. More recently, Ciftci et al. have developed a method to introduce DNA into mammalian cells using a polymer based gene delivery system. (Ciftci et al., *Pharmaceutical Res.* 1997, 14, s-639) This method, however only results in an encapsulation efficiency of 33–49%.

In particular, one of the most common techniques for preparation of biodegradable polymer microspheres encapsulating hydrophilic molecules is the double-emulsion solvent evaporation method. Using this technique, the molecule to be encapsulated is placed in aqueous solution while the polymer is dissolved in an organic phase commonly consisting of methylene chloride or ethyl acetate. The two phases (volume organic/volume aqueous=3–20) are emulsified, typically by sonication or homogenization. This primary emulsion is then added to a second aqueous phase and again mixed by homogenization to form the (water-in-oil)-in-water double emulsion. Upon evaporation of the partially water-miscible solvent, the polymer-containing droplets harden to form microspheres which can then be isolated by filtration or centrifugation. Lyophilization removes water from the interior aqueous phase resulting in a dry suspension of the encapsulated material within the polymer matrix. Unfortunately, however, the encapsulation efficiency of DNA into the hydrophobic matrix of PLGA was low (~20%) using this method. Additionally, the use of this method leads to a tendency of plasmid DNA to be converted from its supercoiled state to a nicked or linear state. The preservation of the supercoiled DNA is important because it is known that supercoiled DNA retains the highest level of bioactivity (Xu et al., *Biochem.* 1996, 35, 5616; Yamaizumi et al., *Mol. Cell Biol.* 1983, 3, 511).

Clearly, many of the methods described above still present a problem for DNA therapeutics because of the tendency of DNA therapeutics to degrade during and after the encapsulation process. Specifically, DNA stress induced degradation is encountered during homogenization and lyophilization. Furthermore, the DNA is susceptible to diffusing out of the aqueous phase, thus decreasing the encapsulation efficiency. Therefore, a method of encapsulating DNA based therapeutics that retains the integrity of the DNA (maximizes the supercoiled-DNA content) and increases the encapsulation efficiency would be desirable.

SUMMARY OF THE INVENTION

Recognizing the need to develop improved delivery systems, the present invention provides methods for the formulation of high supercoiled-DNA content systems and microspheres. In one aspect, the present invention provides a method for the formulation of a high supercoiled DNA content system including formulating an emulsion having a polymer dissolved in organic solvent surrounding an aqueous inner phase containing DNA, and lowering the temperature of the emulsion below the freezing point of the aqueous inner phase. In another aspect, the method includes the step of removing the organic solvent and removing water from the aqueous inner phase to form the system. The system may include microspheres or another implantable structure.

In yet another aspect the invention provides a method for the formulation of high supercoiled DNA content microspheres which increases the encapsulation efficiency of DNA in microspheres and also prevents the degradation of supercoiled DNA during and after formulation, specifically during the homogenization and lyophilization processes. This method includes the formulation of a primary emulsion, and subsequently lowering of the temperature of the primary emulsion below the freezing point of the aqueous inner phase. Finally, the primary emulsion is transferred to a water-based surfactant solution and subjected to homogenization to form a secondary microsphere emulsion. Stirring of the secondary emulsion allows the removal of the organic phase and hardening of the microspheres, which are then isolated, frozen and lyophilized.

In yet another aspect of the invention, a primary emulsion is formed which contains a DNA nicking inhibitor in addition to DNA and buffer. The presence of the DNA nicking inhibitor ensures that the integrity of the DNA is retained. The primary emulsion thus formed with the DNA nicking inhibitor can be utilized in each of the methods described above to provide systems and microspheres with increased encapsulation efficiency and DNA integrity.

In still another aspect, the present invention provides a method for the cryopreparation of water soluble low molecular weight compounds to increase their encapsulation efficiency.

BRIEF DESCRIPTION OF THE DRAWINGS

A description of the invention is made with reference to the Drawing, in which:

FIG. 4 depicts the effect of excipients on retaining supercoiled DNA under microsphere procedure such as homogenization and lyophilization FIG. 5 depicts the effect of homogenization rate, cryopreparation and addition of EDTA on remaining supercoiled DNA FIG. 6 depicts the effect of excipients on retaining supercoiled DNA FIG. 7 depicts the effect of lyophilization on retaining supercoiled DNA

FIG. 10 depicts the analytical methods employed for DNA structure analysis

DETAILED DESCRIPTION OF THE INVENTION

Recognizing the need to retain the integrity and increase the encapsulation efficiency of DNA, the present invention provides methods for the formation of high supercoiled DNA content systems and microspheres. In general, the present invention utilizes a cryopreparation method in which a primary emulsion having an aqueous inner phase and a surrounding organic phase is first formed, and subsequently the temperature of the primary emulsion is lowered below the freezing point of the aqueous inner phase. In another aspect, the present invention also provides a method for the formulation a high supercoiled DNA content system in which, in addition to the cryopreparation method described above, the organic solvent from the surrounding organic phase is removed and the water is removed from the aqueous inner phase to formulate the high supercoiled DNA content system. In yet another aspect, the inventive method also provides for the formulation of high supercoiled DNA content micrspheres by formulating a primary emulsion comprising a polymer dissolved in organic solvent surrounding an aqueous inner phase containing DNA, lowering the temperature of the primary emulsion below the freezing point of the aqueous inner phase, forming a secondary microsphere emulsion and forming the DNA content microspheres.

The present invention also provides, for each of the methods described above, the use of a DNA nicking inhibitor in addition to DNA and buffer in the formation of the primary emulsion. The use of a DNA nicking inhibitor is particularly preferred for each of the methods described above because the presence of the DNA nicking inhibitor ensures that the integrity of the DNA is retained. Once the primary emulsion is formed with the DNA nicking inhibitor, the resulting primary emulsion can then be utilized in each of the methods described above.

In still another aspect of the invention, the encapsulation efficiency of water soluble low molecular weight compounds such as peptides or hormones is increased by the cryopreparation step employed after formation of the primary emulsion. As mentioned above, the cryopreparation step decreases the ability of the water soluble low molecular weight compound to diffuse out of the aqueous phase. The cryopreparation step for water soluble molecular weight compounds is performed similarly to that for the cryopreparation step for DNA as described below.

Description of the Method of the Invention

Although the present invention is described with reference to a method incorporating a DNA nicking inhibitor to form high supercoiled-DNA content microspheres (see example 3), one of ordinary skill in the art will realize that the general method will apply to each of the inventive systems and microspheres (see example 1).

Figure 1:
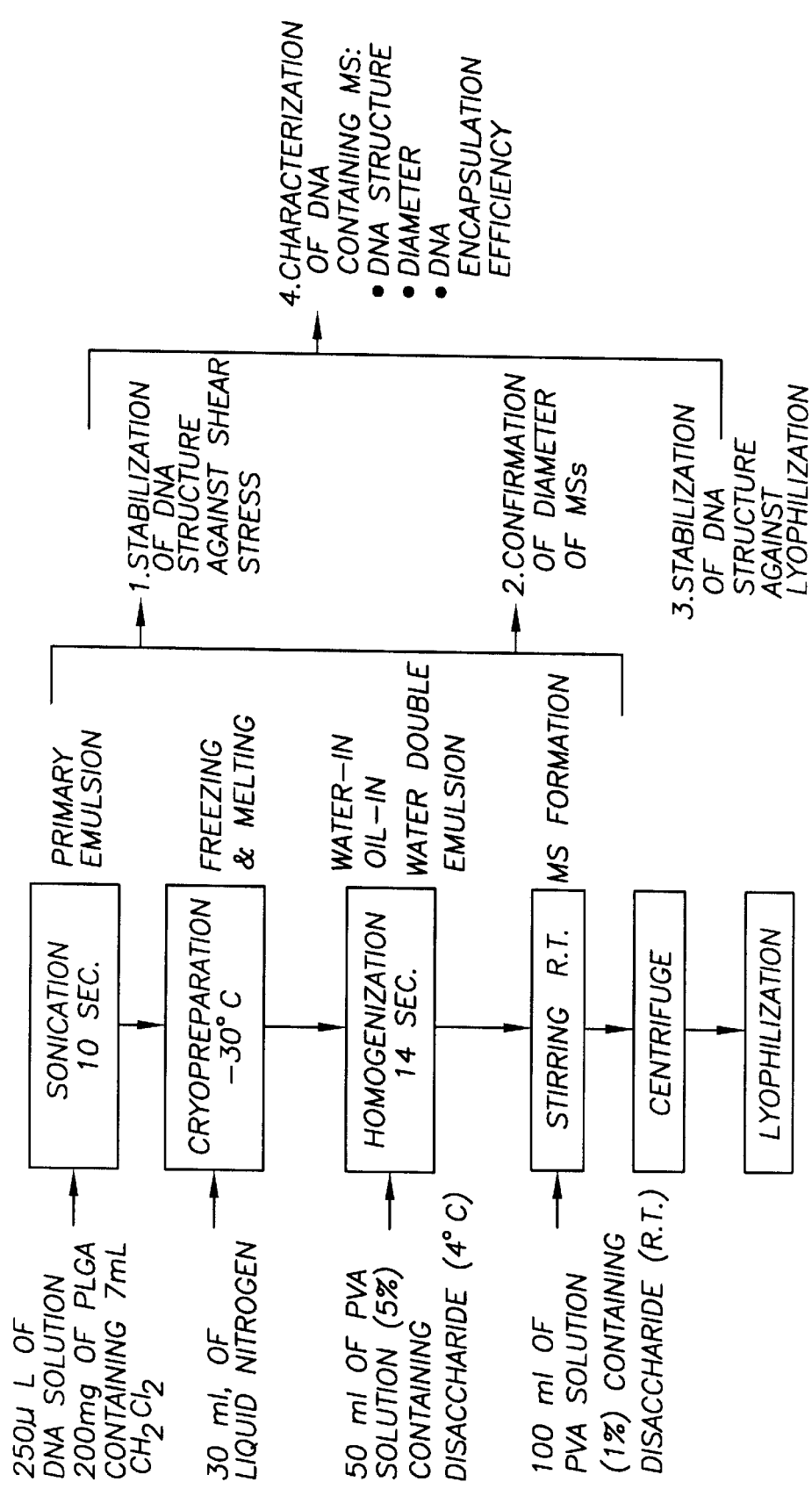
FIG. 1 represents a summary of the microsphere manufacturing procedure

Specifically, the method of the invention is described with reference to the flow diagram of FIG. 1, which shows the microsphere manufacturing procedure. In the method of the invention, the primary emulsion is prepared according to standard methods and consists of a polymer dissolved in an organic solvent and surrounds an aqueous inner phase containing DNA and a DNA nicking inhibitor. In one embodiment of the invention, poly(lactic-co-glycolic)acid is the polymer used and the organic solvent is methylene chloride. It will be appreciated by those of ordinary skill in the art that other polymers and organic solvents may be used according to the method of the presently claimed invention. Other wall-forming materials include, but are not limited to, poly (lactide), poly(glycolide), poly(caprolactone) poly (orthoesters) and poly(hydroxybutyrate). Other solvents may be chosen by one of ordinary skill in the art with the limitation that the solvent must dissolve the wall material and also that the solvent have limited solubility in the extraction medium. One example of a preferred solvent is ethyl acetate. In a preferred embodiment of the present invention, a DNA nicking inhibitor is employed in the presence of a chelator such as EDTA or DTPA. A suitable concentration of EDTA is above 0.5 mM. In another embodiment of the invention, the DNA nicking inhibitor is employed alone. Preferred DNA nicking inhibitors to be used in the claimed invention include carbohydrates, disaccharides, higher molecular weight saccharides, or water soluble polymers. Specific carbohydrates include, but are not limited to, fructose, erythrose, threose, ribose, arabinose, xylose, lyxose, allose, altrose, glucose, mannose, gluose, idose, galactose, erythrulose, ribulose, xylulose, psicose, fructose, sorbose, tagatose, fructofuranose, ribofuranose, ribose, deoxyribose, mannitol, and sialic acid. Specific disaccharides include but are not limited to sucrose, lactose, maltose, cellobiose, trehalose, and lactulose. Specific polysaccharides include but are not limited to starch, glycogen, cellulose, chondroitin, keratin, haparin, dermatan, and haluronic acid. Specific water soluble polymers include but are not limited to polyethylene oxide and polyethylene glycol. The concentration of the DNA nicking inhibitors is preferably in the range of 100–300 mM, and most preferably about 300 mM. Specifically, concentrations of more than 100 mM can be utilized in the present invention, with the limitation that the saccharide must still be soluble.

Once the desired primary emulsion is formed, most preferably by sonication, the primary emulsion temperature is then lowered below the freezing point of the aqueous inner phase. In a preferred embodiment, the temperature of the primary emulsion is lowered by submersion into liquid nitrogen. Other methods of lowering the temperature of the primary emulsion include immersion of the primary emulsion (contained in a sealed vessel) into a solution of dry ice and acetone.

Figure 2:
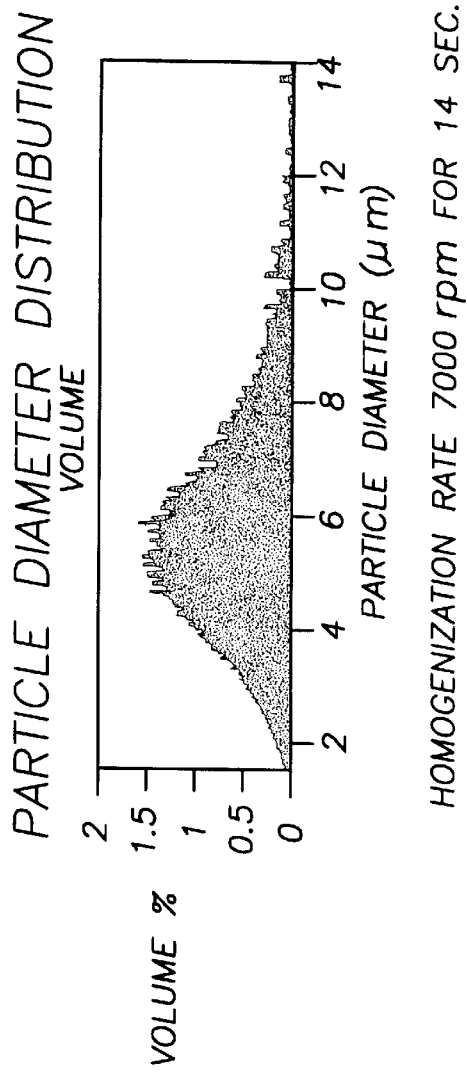
FIG. 2 depicts the effect of homogenization rate on the diameter of microspheres

In a preferred embodiment, the organic phase is then melted until the suspension reaches −30° C. Temperatures in the range of −50° C. to −10 ° C. may also be employed in this step. In a preferred embodiment, the water-based surfactant solution is a solution of 5% polyvinyl alcohol containing 300 mM lactose. It will be appreciated by those of ordinary skill in the art that other water based surfactant solutions include but are not limited to carboxymethyl cellulose, gelatin, poly(vinylpyrrolidone), Tween 80, and Tween 20. In preferred embodiments, the secondary emulsion is formed using homogenization preferably at a range of 5,000 to 9,000 RPM for 14 seconds. The homogenization occurs most preferably at about 7000 RPM. It will be appreciated by one of ordinary skill in the art that the desired size of the spheres depends upon the rate of the homogenization. FIG. 2 shows the effect of the homogenization rate on the diameter of the microspheres. For the purposes of the present invention, spheres with a size of approximately 5 microns are desired, because of the ability of microspheres of this size to enter into phagocytic cells and deliver the therapeutic agent. After homogenization, the microspheres are formed in one embodiment by adding the secondary emulsion to a surfactant solution such as polyvinyl alcohol (most preferably 1%) in 300 mM lactose, and stirred for at least 3 hours at room temperature to remove the methylene chloride. In preferred embodiments, microspheres are collected by centrifugation, washed with distilled water and lyophilized for 15 hours.

Characteristics of Microspheres

Figure 3:
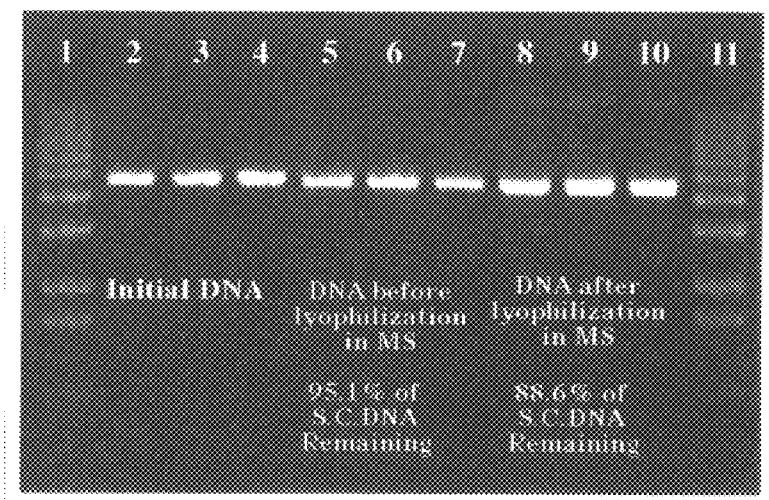
FIG. 3 depicts agarose gel electrophoresis of DNA in microspheres

In preferred embodiments, the collected microspheres described above preferably have mean diameters of less than 1 mm, and more preferably less than 10 microns, and most preferably about 4.8 microns. Additionally, the microspheres contain most preferably greater than 88% of the supercoiled DNA (FIGS. 3 and 4). Moreover, the encapsulation efficiency is most preferably about 89%. For the purposes of the present invention encapsulation efficiency is determined by comparing the amount of DNA initially used with the amount of DNA actually encapsulated.

In comparison, using the standard double-emulsion preparation method (5000 rpm homogenization rate), the resulting microspheres had a mean volume diameter of 4.5 μm, a remaining supercoiled-DNA content of 39%, and a DNA encapsulation efficiency of 23%. It is apparent that cryopreparation prevents degradation of DNA and increases the encapsulation of DNA. These results suggest that the increase in DNA encapsulation efficiency is caused by preventing its diffusion out of the inner aqueous phase by freezing the primary emulsion. Furthermore, addition of DNA-nicking inhibitors to the DNA solution is important to prevent DNA degradation during this microsphere manufacturing process. Ninety-five percent of supercoiled DNA was retained before lyophilization and 88% of supercoiled DNA was retained after lyophilization as shown in FIG. 3. In addition, FIG. 4 compares the supercoiled DNA content in microspheres using water, EDTA, PBS, or lactose in the DNA solution.

Stability of DNA Structure against, Shear Stress

As discussed above, in the cryopreparation method, the aqueous phase of the primary emulsion is frozen. Since the shear stress inside a solid equals zero, it is expected that cryopreparation would help to preserve the supercoiled DNA during homogenization. This is supported by the results depicted in FIG. 5 which indicates that the supercoiled-DNA content decreases with an increase in homogenization rate, and that using the cryopreparation method preserves the supercoiled-DNA content. These results suggest that freezing the inner DNA solution protects the DNA from degradation by shear stress, and suggests that cryopreparation is a useful method to prevent supercoiled DNA from degrading during microsphere preparation. When ethylenediaminetetraacetic acid (EDTA) was added to the DNA solution, the supercoiled-DNA DNA content of the resulting microspheres was significantly higher than in the absence of EDTA. EDTA is a chelator of divalent metal cations and inhibits the activity of DNase by this mechanism. This activity of EDTA suggests that the stability of DNA in the presence of EDTA may be due to DNase inhibition. In order to examine this possibility of calcium-dependent DNase-mediated degradation, a calcium ionophore (N, N, N', N'-tetracyclohexyldiglycolic diamide was also included (calcium ionophore II, log $K_{Ca}$=10.1, $\mu$=0.1, 20°C.) instead of EDTA (log $K_{Ca}$=11.0, $\mu$=0.1, 20° C.). As shown in FIG. 6, it is apparent that the calcium ionophore II did not act as a DNA stabilizer. Therefore, it is likely that the mechanism of DNA stabilization during cryopreparation is not a result of calcium-dependent DNase inhibition. In addition, FIG. 6 indicates that DNA degradation during cryopreparation was not inhibited by the addition of PBS (1 mM $K_2HPO_4$, 10 mM $Na_2HPO_4$, 137 mM NaCl, 2.7 mM KCl pH 7.0), Tris, or lactose to the DNA solution. In the case of addition of PBS or Tris to the DNA solution containing unbuffered EDTA, the supercoiled-DNA content was increased from 75% to 95%. The exact mechanism of DNA stabilization is unknown. However, it is apparent that the presence of both lactose and EDTA in the DNA solution is important for the stabilization of supercoiled DNA against degradation during cryopreparation.

Stability of DNA Structure during Lyophilization

Figure 8:
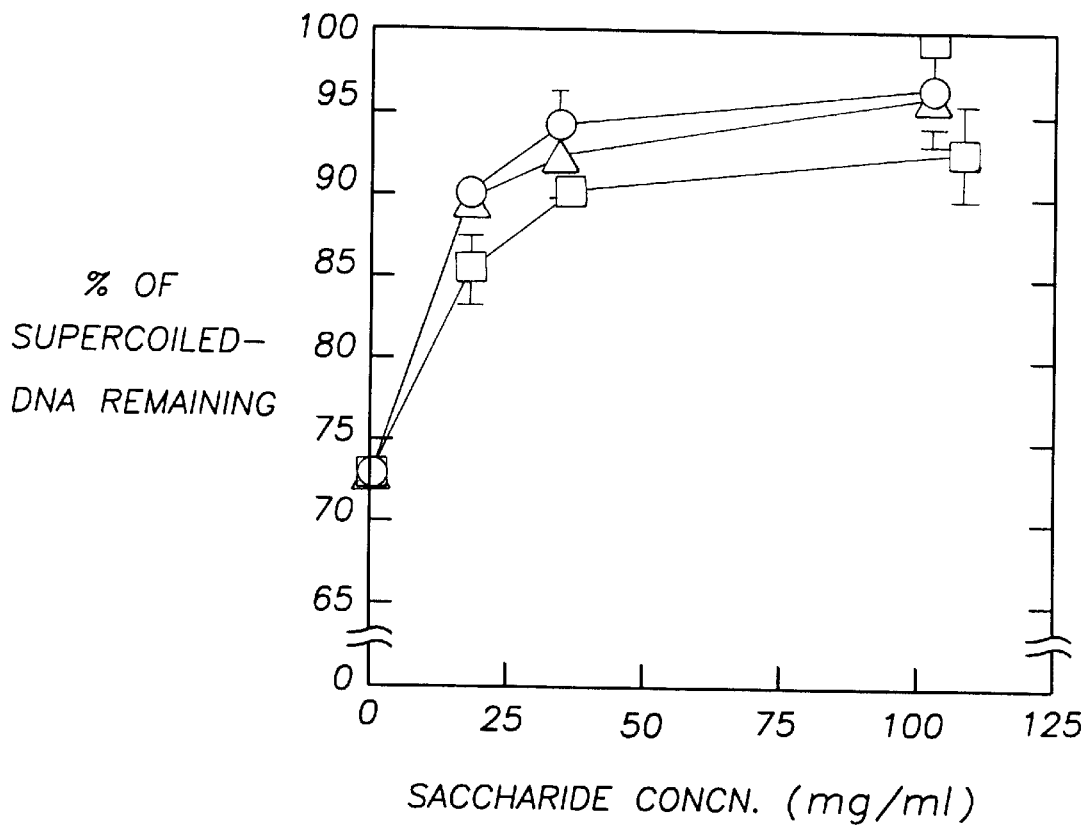
FIG. 8 depicts the effect of saccharides on DNA stability during lyophilization

DNA samples were directly lyophilized to study the effect of lyophilization on DNA stability. FIG. 7 indicates that the DNA stability in 300 mM lactose and in 1 mM EDTA was the same as that of DNA in water. On the other hand, when Tris buffer or PBS was used in the DNA solution, DNA degradation was increased. Salts such as sodium phosphate are known to form crystals upon freezing and it was speculated that DNA nicking was caused by the salt crystallization. (In the presence of 1 mM EDTA, however, the salt concentration might not be high enough to degrade DNA by its crystallization) Saccharides are known cryoprotectants for proteins during lyophilization, and it was reasoned that they may protect DNA in similar fashion. Therefore, the effect of saccharides on DNA stability upon lyophilization from TE buffer was examined. FIG. 8 indicates that the DNA degradation was decreased with an increase in the amount of saccharide. Other disaccharides such as maltose, trehalose, and cellobiose showed DNA stabilization similar to the effect of lactose. The addition of saccharides in the inner aqueous phase of the primary emulsion improved the supercoiled DNA content of the microspheres, as well. Note that the concentrations of glucose are 100, 200 and 600 mM while those of sucrose and lactose are 50, 100 and 300 mM. This indicates that DNA stability depends on the total mass of saccharide and not the molar concentration of sugar.

Figure 9:
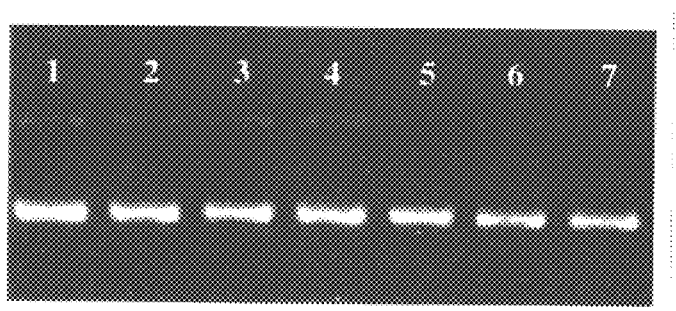
FIG. 9 depicts agarose gel electrophoresis of DNA incubated at room temperature in PBS at pH 7.4

Acidic pH is also known to damage DNA by depurination (Suzuki et al., *Nucleic Acids Res.* 1994, 22, 4997). Freezing of sodium phosphate buffer, initially at pH 7.0 may result in pH as low as 4.0, and this process could potentially contribute to the observed plasmid degradation. However, DNA which was incubated for up to 60 min at room temperature in PBS (FIG. 9) or TE (10 mM Tris/1 mM EDTA) showed no degradation at either pH 7.4 or pH 4.0 (Szkudlarek et al., *Abstr. Pap. Am. Chem. Soc.* 1996, 211, 38-BIOT). Thus, it is believed that any pH changes in the solution upon freezing have negligible effect on the DNA stability during microsphere preparation.

The presently claimed invention is exemplified below, however, these examples are not intended to limit the scope of the presently claimed invention.

EXAMPLES

MATERIALS

Plasmid DNA (pCMV-β-gal) was purified from *E. coli* (DH5α) using Plasmid Mega Kit column isolation (QIAGEN, Calif.), followed by ethanol precipitation. Poly (d,l-lactic-coglycolic acid) (PLGA), with a comonomer ratio of 50:50 and an inherent viscosity n=0.4 (Resomer RG503, MW 31,000) was purchased from Boehringer Ingelheim (Gerrnany). The emulsifier, poly(vinyl alcohol) (PVA) (88 mol % hydrolyzed, MW 25,000), was purchased from Polysciences, Inc. (Warrington, Pa.). All other chemicals used were of the highest grade commercially available.

Example 1

Crypreparation: DNA containing microspheres were prepared using a cryopreparation method based on the water-in-oil-in-water double emulsion solvent-evaporation method. The two phases, consisting of 250 µm of DNA solution (250 µg of DNA) and 7 mL of methylene chloride containing 200 mg of PLGA, were emulsified by sonication for 10 s (ultrasonic probe, Sonic & Materials, Inc.) At room temperature. The primary emulsion temperature was then lowered below the freezing point of the aqueous inner phase by liquid nitrogen immersion, and 50 mL of a 5% PVA solution (4–7° C.) was added and homogenized at 5000–9000 rpm for 14 s (Silverson L4R homogenizer). After homogenization, the resulting emulsion was diluted in 100 mL of 1% PVA, and the system was stirred magnetically for 3 h to allow for evaporation of the organic solvent. Microspheres were finally collected by centrifugation and washed 3 times with water to remove excess PVA. Note that all of the PVA solutions were adjusted to the osmotic pressure of the inner aqueous phase using agents such as saccharides. The microspheres were resuspended in approximately 1 mL of water, frozen in liquid nitrogen, and lyophilized at room temperature for 24 h on a Labconco Freeze-Dryer 8.

Example 2

Achieving DNA Stability against Lyophilization Using Excipients: The effect of lyophilization on DNA was studied by directly lyophilizing DNA samples (20 µg/mL). Aliquots (1 mL each) of the DNA solutions, with or without excipients, were frozen in 20 mL disposable scitillation vials by liquid nitrogen immersion and immediately lyophilized at room temperature for 15 h.

Example 3

Optimized Microsphere Preparation: The two phases, consisting of 250 µL of DNA in water (750 µg of DNA) containing 1 mM EDTA and 300 mM lactose (pH 7.0) and 7 mL of methylene chloride containing 200 mg of PLGA, were emulsified by sonication as described above. After the primary emulsion was cryoprepared, 50 mL of 5% PVA solution containing 300 mM lactose was added to the solution and homdouble emulsion was then diluted in resulting double emulsion was then diluted in 100 mL of 1% PVA solution with 300 mM lactose, and the system was stirred magnetically for 3 h to allow the evaporation of the organic solvent. Microspheres were finally collected by centrifugation, washed three times with distilled water, and then lyophilized at room temperature to obtain a powder.

Example 4

Analysis of DNA Structure: The DNA structure was analyzed by agarose gel elecrophoresis (1% agarose containing ethidium bromide, 110 V, 90 min) and compared to untreated stock DNA for semiquantitative determination of supercoiled-DNA content using a BioRad Gel Doc 1000 (Software, Molecular Analyst 2.1). As shown in FIG. 10, each DNA band was integrated as a volume. Supercoiled DNA (SC DNA) content was defined as the volume integrated from the supercoiled DNA band over the total volume inntegrated from all bands. In other words, SC DNA content eqals (SC DNA volume−background volume)/[SC DNA volume+linear volume+nicked DNA volume−(3× background volume)]. SC DNA content remaining after preparation was calculated as follows: SC DNA remaining (initial %)=100×(SC DNA content of sample DNA)/(SC DNA content of initial DNA).

Example 5

Quantitation of DNA Content in Microsphere: The microsphere DNA content was determined using fluorescent reagent PicoGreen (Molecular Probes, Eugene, Oreg.) which preferentially binds to double stranded DNA and to a lesser extent to single stranded DNA. Fluroescence (lex–480 nm, 1=520 nm) of extracted DNA was compared to a standard curve, using plasmid DNA, which was linear from 1 to 50 ng/mL. The encapsulation efficiency was determined as the amount of DNA recovered from the microspheres relative to the initial amount of DNA used (encapsulation efficiency=100×(DNA recovered)/(initial DNA)].

Example 6

Particle Size of Microsphere: Particle size distribution of microspheres was analyzed by a Coulter Multisizer II (Coullter Electronics Inc., Hialeah, Fla.), and the mean volume diameter distribution was determined.

What is claimed is:

1. A method for the formulation of a high supercoiled DNA content system comprising:

formulating an emulsion comprising a polymer dissolved in organic solvent surrounding an aqueous inner phase containing DNA; and lowering the temperature of the emulsion below the freezing point of the aqueous inner phase to form the system.

2. A method for the formulation of a high supercoiled DNA content system comprising:

formulating an emulsion comprising a polymer dissolved in organic solvent surrounding an aqueous inner phase containing DNA;

lowering the temperature of the emulsion below the freezing point of the aqueous inner phase; and removing the organic solvent and removing water from the aqueous inner phase to form the high supercoiled DNA content system.

3. A method for the formulation of high supercoiled DNA content microspheres comprising:

formulating a primary emulsion comprising a polymer dissolved in organic solvent surrounding an aqueous inner phase containing DNA;

lowering the temperature of the primary emulsion below the freezing point of said aqueous inner phase;

forming a secondary microsphere emulsion; and forming the high supercoiled DNA content microspheres.

4. The method of claim 3, wherein forming a secondary microsphere emulsion comprises:

transferring the primary emulsion to a water-based surfactant solution; and homogenization of the primary emulsion and the water-based surfactant.

5. The method of claim 3, wherein forming the microspheres comprises removal of the organic phase and hardening of the microspheres.

6. The method of claim 5, wherein removal of the organic phase comprises evaporation of the organic solvent.

7. The method of claim 1 or 2, wherein the system comprises microspheres.

8. The method of claim 1 or 2, wherein the system comprises an implantable structure.

9. The method of claim 3, further comprising isolation of the microspheres.

10. The method of claim 9, wherein isolation of the microspheres comprises:
centrifuging the microspheres;
freezing the microspheres in liquid nitrogen; and
lyophilizing the microspheres.

11. The method of claims 1, 2 or 3, wherein said wall-forming polymer is selected from the group consisting of poly(lactic-co-glycolic) acid, polyethylene glycol, polyethylene oxide, poly(caprolactone), poly(lactide), poly(glycolide), poly(orthoesters), and poly(hydroxybutyrate).

12. The method of claims 1, 2, or 3, wherein the aqueous inner phase further includes a chelator and a DNA nicking inhibitor.

13. The method of claim 12, further comprising a buffer.

14. The method of claim 12, wherein said chelator is EDTA or DTPA, and wherein said nicking inhibitor is selected from the group consisting of carbohydrates, disaccharides, higher molecular weight saccharides and water-soluble polymers.

15. The method of claim 14, wherein the carbohydrate is selected from the group consisting of fructose, erythrose, threose, ribose, arabinose, xylose, lyxose, allose, altrose, glucose, idose, galactose, erythrulose, ribulose, xylulose, psicose, fructose, sorbose, tagatose, fructofuranose, ribofuranose, ribose, deoxyribose, manitol, and sialic acid.

16. The method of claim 14, wherein the disaccharide is selected from the group consisting of sucrose, lactose, maltose, cellobiose, trehalose and lactulose.

17. The method of claim 14, wherein the polysaccharide is selected from the group consisting of starch, glycogen, cellulose, chondroitin, keratin, haparin, dermatan, and haluronic acid.

18. The method of claim 14, wherein said water-soluble polymer comprises polyethylene oxide or polyethylene glycol.

19. The method of claim 12, wherein the concentration of said DNA nicking inhibitor is preferably greater than 100 nM.

20. The method of claim 12, wherein the concentration of DNA nicking inhibitor is preferably in the range of 100 nM to 300 nM.

21. The method of claim 12, wherein the concentration of DNA nicking inhibitor is preferably about 300 nM.

22. The method of claim 13, wherein said chelator is EDTA or DTPA, and wherein said nicking inhibitor is selected from the group consisting of carbohydrates, disaccharides, higher molecular weight saccharides and water-soluble polymers.

23. The method of claim 22, wherein the carbohydrate is selected from the group consisting of fructose, erythrose, threose, ribose, arabinose, xylose, lyxose, allose, altrose, glucose, idose, galactose, erythrulose, ribulose, xylulose, psicose, fructose, sorbose, tagatose, fructofuranose, ribofuranose, ribose, deoxyribose, manitol, and sialic acid.

24. The method of claim 22, wherein the disaccharide is selected from the group consisting of sucrose, lactose, maltose, cellobiose, trehalose and lactulose.

25. The method of claim 22, wherein the polysaccharide is selected from the group consisting of starch, glycogen, cellulose, chondroitin, keratin, haparin, dermatan, and haluronic acid.

26. The method of claim 22, wherein said water-soluble polymer comprises polyethylene oxide or polyethylene glycol.

27. The method of claim 13, wherein the concentration of DNA nicking inhibitor is preferably greater than 100 nM.

28. The method of claim 13, wherein the concentration of DNA nicking inhibitor is preferably in the range of 100 mM to 300 mM.

29. The method of claim 13, wherein the concentration of DNA nicking inhibitor is preferably about 300 mM.

30. A high supercoiled DNA content microsphere comprising a wall-forming polymeric material, DNA, buffer, chelator, and a DNA nicking inhibitor, wherein said microsphere is formed by a method comprising the steps of:
formulating a primary emulsion comprising a polymer dissolved in organic solvent surrounding an aqueous inner phase containing DNA;
lowering the temperature of the primary emulsion below the freezing point of said aqueous inner phase;
forming a secondary microsphere emulsion; and
forming the high supercoiled DNA content microspheres.

31. A high supercoiled DNA content microsphere comprising a wall-forming polymeric material, DNA, chelator, and a DNA nicking inhibitor, wherein said microsphere is formed by a method comprising the steps of:
formulating a primary emulsion comprising a polymer dissolved in organic solvent surrounding an aqueous inner phase containing DNA;
lowering the temperature of the primary emulsion below the freezing point of said aqueous inner phase;
forming a secondary microsphere emulsion; and
forming the high supercoiled DNA content microspheres.

32. A high supercoiled DNA content microsphere having a mean diameter less than 10 microns, containing over 88% of the supercoiled DNA and having an encapsulation efficiency of about 89%, wherein said microsphere is formed by a method comprising the steps of:
formulating a primary emulsion comprising a polymer dissolved in organic solvent surrounding an aqueous inner phase containing DNA;
lowering the temperature of the primary emulsion below the freezing point of said aqueous inner phase;
forming a secondary microsphere emulsion; and
forming the high supercoiled DNA content microspheres.

* * * * *